(12) United States Patent
Heisel

(10) Patent No.: US 6,676,906 B1
(45) Date of Patent: Jan. 13, 2004

(54) REACTOR FOR CARRYING OUT REACTIONS HAVING A HIGH ENTHALPY CHANGE

(75) Inventor: Michael Heisel, Gistlstrasse 54, Pullach (DE), 82049

(73) Assignee: Michael Heisel, Pullach (DE)

( * ) Notice: Subject to any disclaimer, the term of this patent is extended or adjusted under 35 U.S.C. 154(b) by 0 days.

(21) Appl. No.: 09/435,355

(22) Filed: Nov. 8, 1999

(30) Foreign Application Priority Data

Nov. 6, 1998 (DE) .......................... 198 51 109

(51) Int. Cl.[7] .................. B01J 8/00; B01J 8/02
(52) U.S. Cl. .............. 422/190; 422/191; 422/193; 422/198; 422/200; 422/211
(58) Field of Search ............... 422/190, 191, 422/198, 196, 197, 200, 201, 204

(56) References Cited

U.S. PATENT DOCUMENTS 1,330,003 A * 2/1920 Radison et al. ............ 422/197
3,127,247 A * 3/1964 Davis, Jr. .................. 422/188
4,544,544 A * 10/1985 Dang Vu et al. ........... 423/659

FOREIGN PATENT DOCUMENTS

WO      WO 98/30856    * 7/1998

* cited by examiner

Primary Examiner—Hien Tran
(74) Attorney, Agent, or Firm—Millen, White, Zelano, Branigan, P.C.

(57) ABSTRACT

The invention relates to a reactor for carrying out reactions having a high enthalpy change containing catalyst particles between cooled dividing walls. According to the invention, the cooled dividing walls are formed by metal plates/metallic components in which hollow or intermediate spaces in the form of channels are provided in the metal plates/components for accommodating and conveying a cooling medium so as to cool the reactor. The reactor can be used for carrying out strongly exothermic catalytic reactions, for example for the selective hydrogenation of acetylene to ethylene.

8 Claims, 6 Drawing Sheets

REACTOR FOR CARRYING OUT REACTIONS HAVING A HIGH ENTHALPY CHANGE

FIELD OF THE INVENTION

The invention relates to a reactor for carrying out reactions having a high enthalpy change containing catalyst particles between cooled dividing walls in at least one reactor vessel.

BACKGROUND OF THE INVENTION

Such a reactor is known from the journal Hydrocarbon Processing, March 1991, page 134. This is a multitube reactor with catalyst particles in the tubes. The tubes are cooled on the jacket side of the reactor by means of boiling water or other suitable heat-transfer media.

The distribution of the reaction space and the catalyst particles over a plurality of tubes ensures that in the case of an operating fault any self-accelerating reaction caused by local overheating is restricted to one reaction tube and does not encompass the entire reactor. This reactor construction has proven itself but has a number of disadvantages.

The reactor wall has to be designed for the coolant pressure, which in practice is often at a high pressure. As a result, the reactor wall is very thick and therefore expensive, difficult to transport and assembly on the construction site is ruled out.

For large diameters, the tube plates are very thick and therefore expensive and prone to damage by thermal stresses.

A great deal of effort is required to weld the many reaction tubes into the thick tube plates.

Filling the many reaction tubes requires a great deal of effort and care. In particulars care must be taken to ensure that the tubes are filled uniformly with the same pressure drop in the various tubes so that a reaction tube through which too little reaction mixture passes because of the high pressure drop is not overheated.

Owing to the high weight, carbon steel is usually used for the reactor, although this makes rust unavoidable. However, rust acts as a catalyst poison for many reactions. For this reason, the reactor has to be sandblasted when the catalyst is removed, and this sandblasting is costly because of the large number of reaction tubes.

Only upright reactors are possible.

The cooling area per catalyst volume can be chosen only within narrow limits.

SUMMARY OF THE INVENTION

It is therefore an object of the invention to achieve a simpler reactor construction combined with a high level of safety in the case of faults during operation and avoidance of the abovementioned disadvantages.

According to the invention, this object is achieved by a reactor for carrying out reactions having a high enthalpy change containing catalyst particles between cooled dividing walls in at least one reactor vessel, characterized in that the cooled dividing walls are formed by means of metal plates/metallic components and hollow or intermediate spaces in the form of channels for accommodating and conveying a cooling medium.

According to the invention, this object is achieved by a reactor for carrying out reactions having a high enthalpy change containing catalyst particles between cooled dividing walls in at least one reactor vessel, characterized in that the cooled dividing walls are formed by means of metal plates/metallic components and hollow or intermediate spaces in the form of channels for accommodating and conveying a cooling medium.

The separate reaction chambers produced by the cooled dividing walls also prevent overheating of adjacent reaction chambers in the event of the abovementioned operating malfunctions. Metal plates/metallic components which can be used according to the invention are commercially available as coolable or heatable panels and make inexpensive solutions for the internal reactor fittings possible.

In an advantageous embodiment of the reactor of the invention, a plurality of metal plates are assembled, preferably vertically, with a spacing between them to give a metal plate pack and thus form a free space into which the catalyst particles are poured. Tube plates are dispensed with and the reaction chambers between the plates are filled like a fixed bed without cooling. This is a substantial improvement over a reactor according to the prior art.

The metal plate packs are advantageously made up of flat, preferably parallel, plates or of cylindrically curved, preferably concentric, plates. Such plates, including plate packs, are commercially available at a relatively low cost.

In a preferred embodiment of the reactor of the invention, a plurality of metal plate packs are arranged next to one another in the reactor vessel in such a way that they form a module of plate packs in which the feed gas flows in parallel through the plate packs. This can be realized easily, particularly also in horizontal vessels. As a result, the limits of constructability are shifted to significantly larger units and low pressure drops are made possible when using the reactor of the invention.

It is also possible for the feed gas to flow through a plurality of modules either in the same reactor vessel, preferably above one another, or in a plurality of reactor vessels, parallel or in series. Combined with the choice between upright and horizontal reactor vessels, the reactor can thus be optimally matched to the available space and the permissible pressure drop in the reactor.

Further advantages of the reactor of the invention result from the combined effect of the features of the invention with those of its advantageous embodiments:

The reactor wall has to be designed only for the pressure of the reaction gas and, for example, not for the higher pressure of the steam which is generated during cooling by vaporizing boiler feed water.

The reactor requires no tube plates and is therefore significantly lighter than a reactor according to the prior art. In addition, the metal plates can be constructed of stainless steel so that the abovementioned problems when using carbon steel do not occur.

The cooling area per catalyst volume can be freely chosen within very wide limits.

Owing to the fact that the reactors of the invention are significantly lighter for the same throughput, transport, installation and foundations are cheaper than in the case of reactors according to the prior art.

Constructability limits and safety considerations do not restrict the production capacity which can be installed at a given location.

In an advantageous use of the reactor of the invention, a highly exothermic catalytic reaction is carried out between the cooled dividing walls of the reactor.

The reactor can be used, for example, in the reaction of acetylene to form ethylene. In this use, the reactor of the invention makes it possible to simplify the process as explained below and at the same time to make the cooled reactor simpler, safer and cheaper and to shift its constructability limits significantly in the direction of larger units.

When using the reactor of the invention, the reaction chambers in the reactor are bounded by cooled dividing walls and cooling is effected by a fluid which flows within the dividing walls in a very simple manner as a result of, according to the invention, the cooled dividing walls in the reactor being made up of metal plates and hollow spaces in the form of channels being provided in the metal plates to accommodate and convey at least one fluid.

The dividing walls form separate reaction chambers for the reaction of acetylene to give ethylene. Should an over-reaction actually occur in one of these reaction chambers, the over-reaction remains restricted to this small space and does not encompass the entire reactor. This very significantly increases production safety and makes it acceptable for the first time to construct reactor units which are significantly larger than those possible according to the prior art.

Since surfaces made of metal plates are cheap to produce, it is possible to make available additional heat-exchange area without incurring high costs. In particular, inert material can be used instead of catalyst at the gas outlet from the reactor, so that although a reaction no longer takes place at this point of the reactor, cooling still takes place by means of the metal plates. This ensures that no hot gas from an over-reaction heats the product gas stream and can likewise trigger the over-reaction there.

Since the plates require little forming or finishing work, there is little restriction in the choice of material. In particular, anticorrosion measures can be realized more easily than in the case of tubes. Particularly high-value and expensive materials such as Hastelloy are more readily available commercially as sheets than as tubes.

Furthermore, the low pressure drop in the reactor of the invention allows the feed gas to flow through the catalyst bed at a higher, space velocity. This increases the selectivity of the catalyst so that the safety margin to an undesired ever-reaction becomes larger.

However, the reactor of the invention is not restricted to this use. Other applications can be deduced in a similar manner from the properties of the reactor. In particular, other reactions having a high enthalpy change can be carried out in this reactor, for example the epoxidation of olefins, CO conversion for production of $H_2$, the direct oxidation of $H_2S$ to elemental sulphur, the Claus reaction, the hydrogenation of hydrocarbons, in particular the selective hydrogenation of hydrocarbons such as the hydrogenation of $C_2H_2$ to $C2H_4$, the oxidation of $SO_2$ to $SO_3$, the synthesis of methanol, the synthesis of methane, the Fischer-Tropsch synthesis and the synthesis of $NH_3$. All these reactions are exothermic. However, the reactor is in principle also suitable for carrying out endothermic reactions. A specific example of this type is the use of the reactor in a Claus plant in which the last reactor is operated below the dew point of sulphur (=sub-dew-point, SDP operation). As described in EP 0 283 193, two reactors are cyclically exchanged in this process and the sulphur-laden reactor is regenerated. At the beginning of this regeneration, a great deal of heat has to be introduced in order to vaporize the sulphur deposited on the catalyst. The reactor of the invention can aid this procedure in that a heating medium, e.g. hot boiler feed water for generating intermediate-pressure steam, is passed into the metal plates so as to heat the reactor quickly and thus drive off the sulphur. In normal operation, the reactor then reheats. When the temperature of the intermediate-pressure steam has been reached, the boiler feed water changes its function from that of a heating medium to that of a cooling medium, i.e. intermediate-pressure steam is then generated by vaporization which cools the reactor.

DETAILED DESCRIPTION OF THE DRAWINGS

Figure 1:
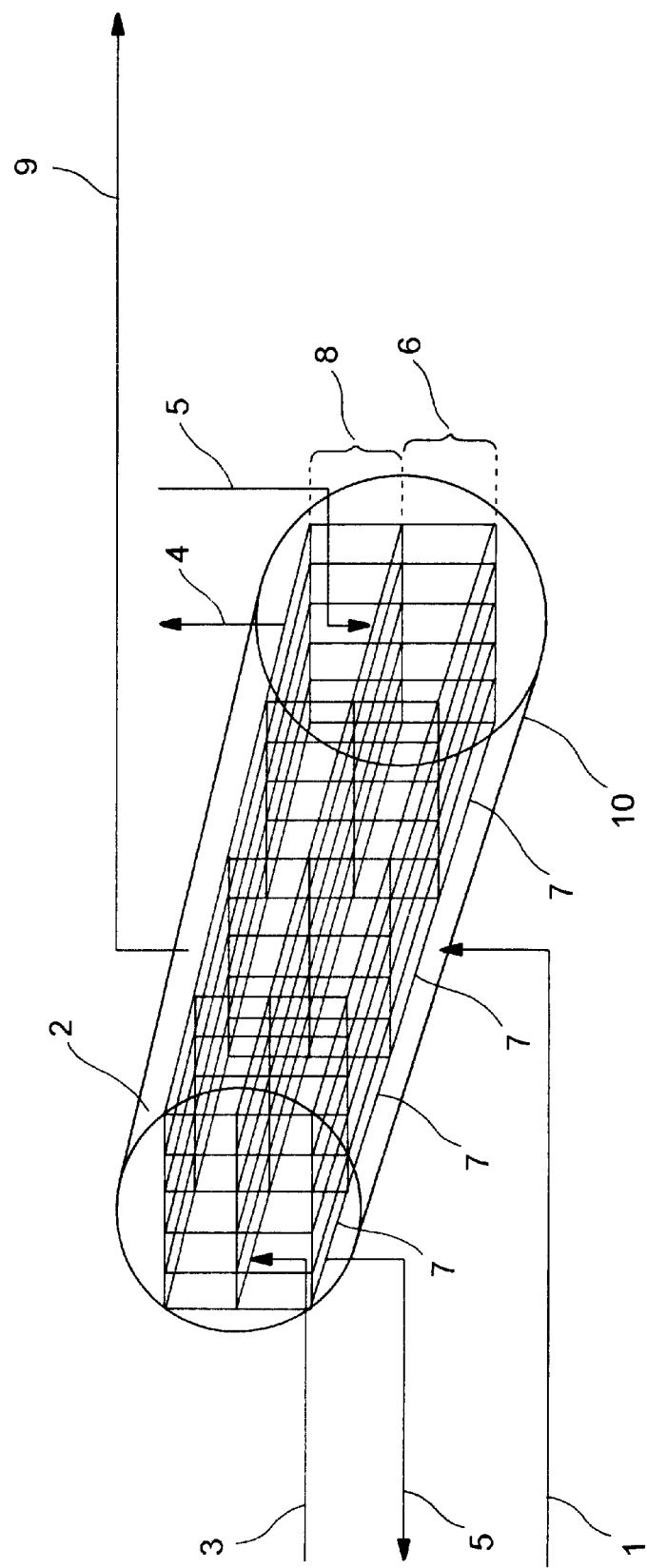
FIG. 1 is a schematic of an horizontal reactor.
Figure 2:
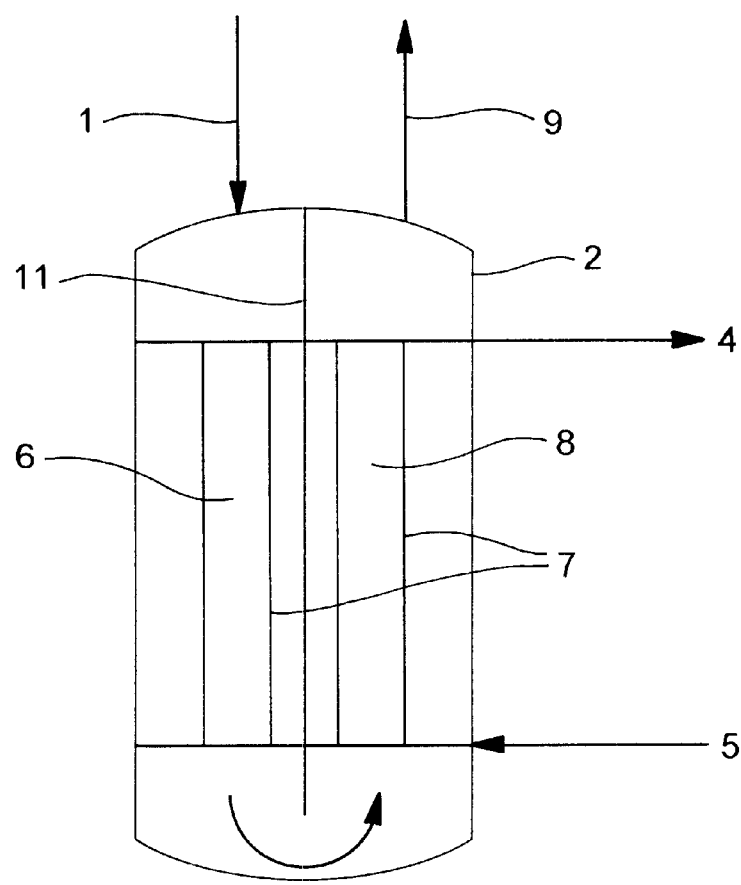
FIG. 2 shows the modules in series.
Figure 2:
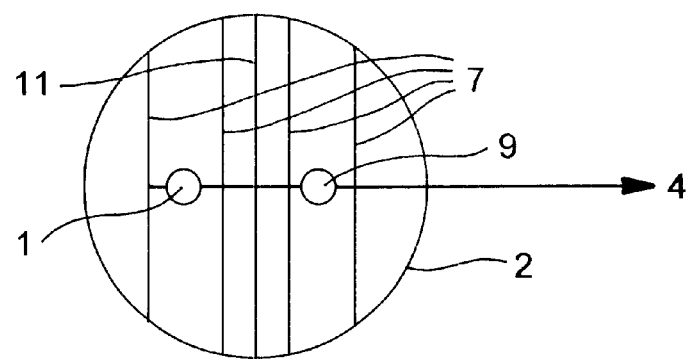
Figure 3:
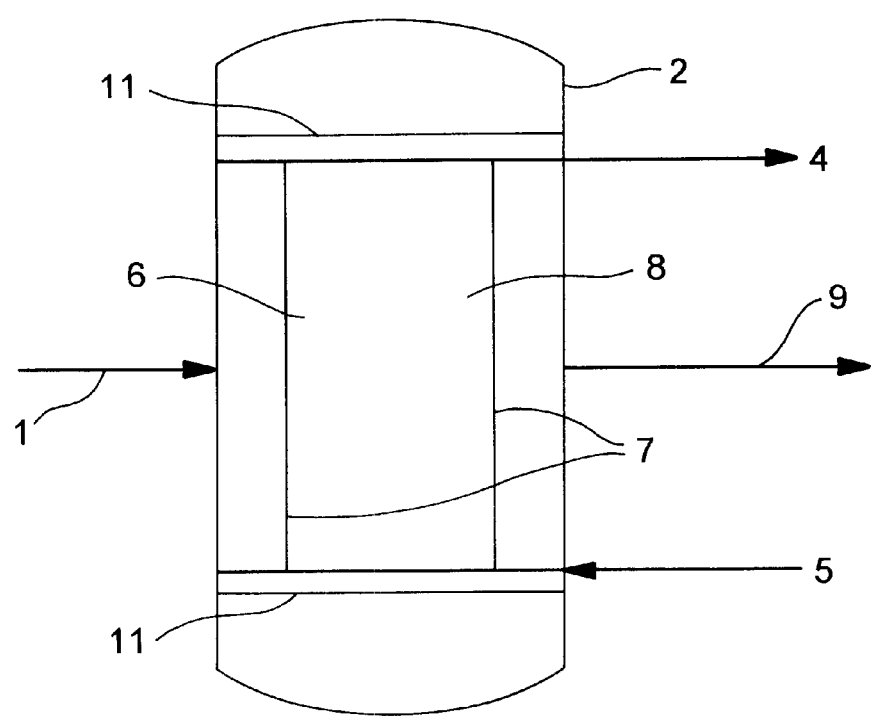
FIG. 3 shows horizontal flow of reaction fluid, vertical flow of sheet transfer fluid.
Figure 3:
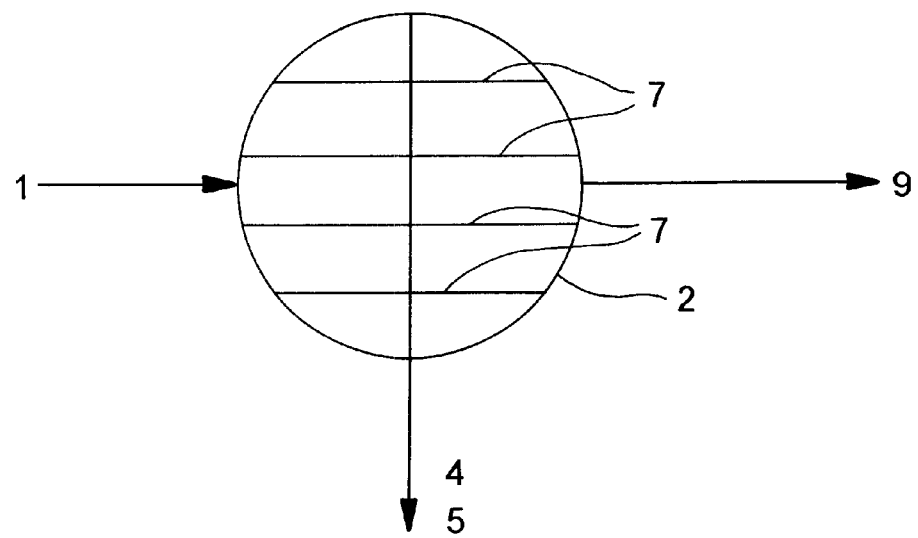
Figure 4:
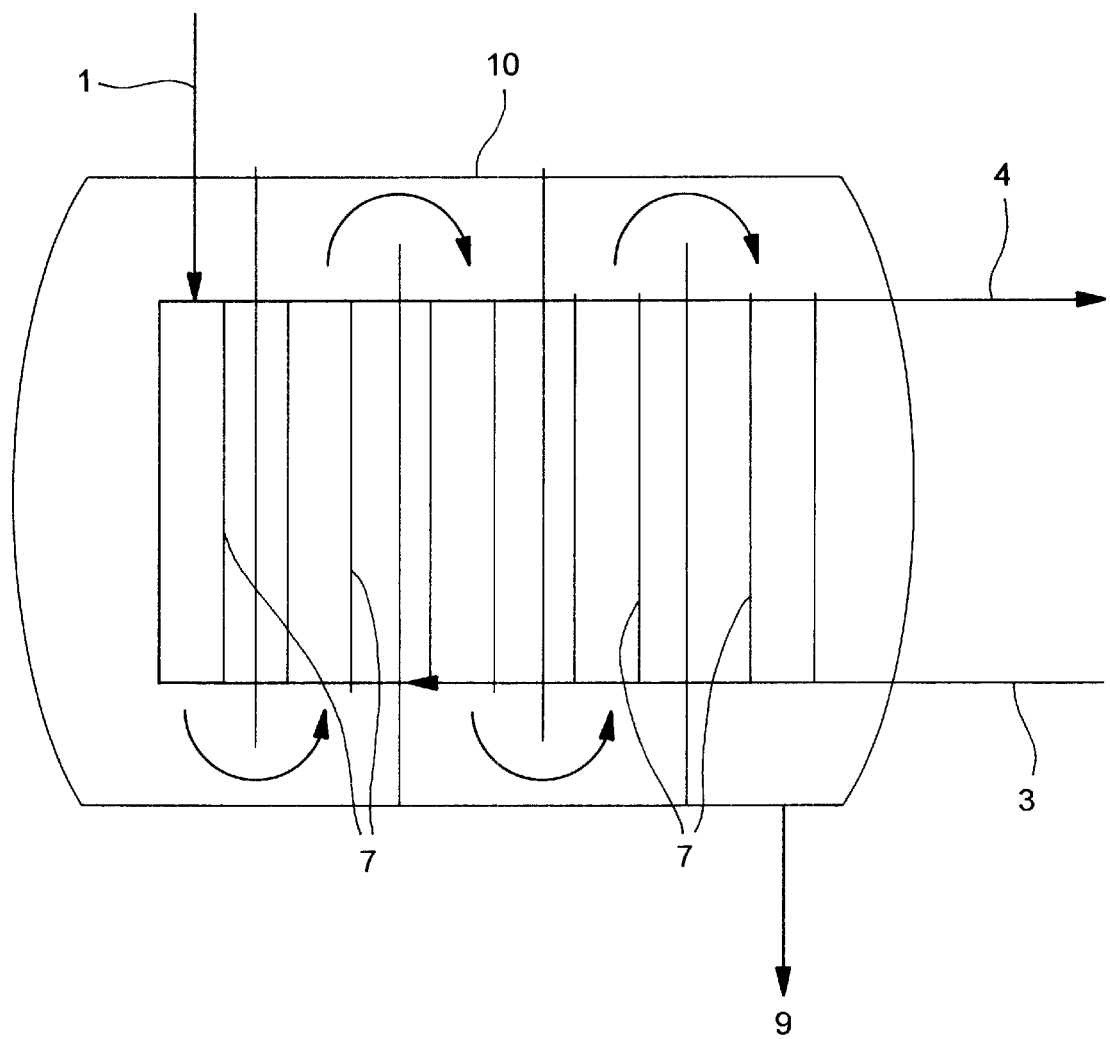
FIG. 4 shows 4 modules in series.
Figure 5:
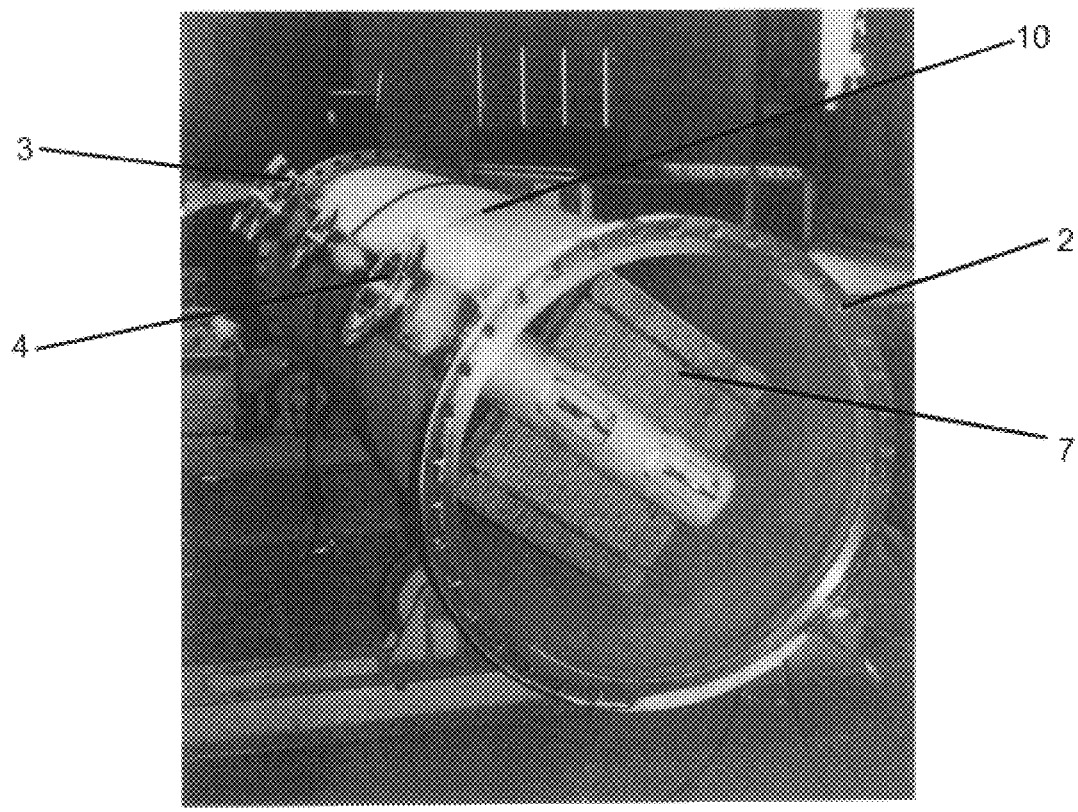
FIG. 5 shows the horizontal arrangement of plates.
Figure 6:
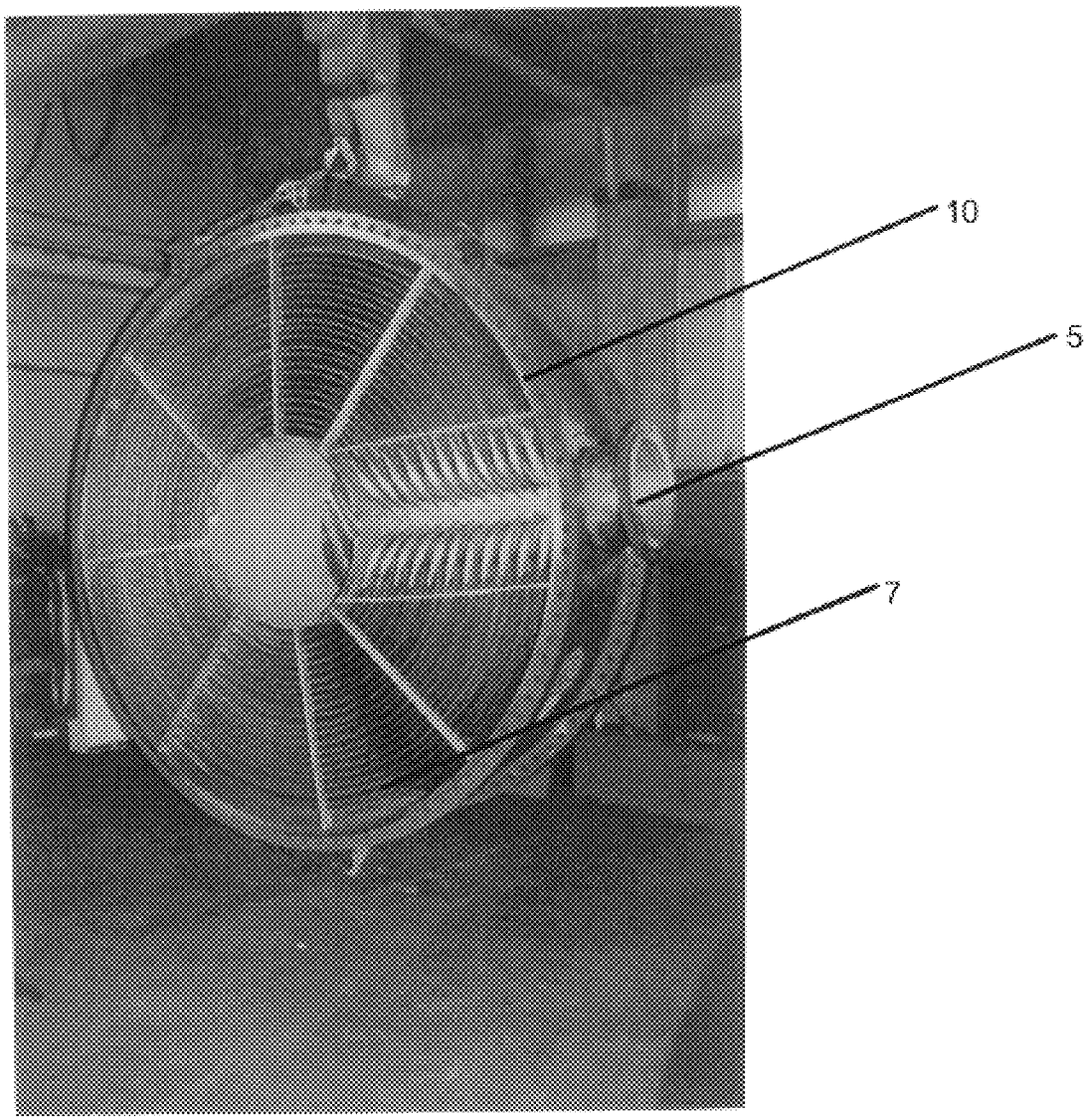
FIG. 6 shows the cylindrical arrangement of plates.

FIG. 1 schematically shows an embodiment of the reactor of the invention and its use in a plant for the selective hydrogenation of acetylene to ethylene. The figure shows a reactor 2 in the form of a horizontal vessel 10 in which two modules 6, 8 of plate packs 7 are arranged. It is indicated that the packs 7 comprise cooled parallel plates whose edges are shown as lines in the figure. The structure of the cooled plates can resemble the radiators in dwellings and offices. The catalyst beds between the plates are not shown in the figure.

In operation, a feed gas is fed to the reactor 2 via line 1 and the reactor can be cooled by means of liquid methanol 3, so that methanol is obtained in vapour form which flows out via line 4. The gas 1 used, e.g. ethylene with small amounts of acetylene and a superstoichiometric amount of hydrogen compared with that required for hydrogenation of acetylene to ethylene, is preheated by means of a heat-transfer medium 5, which can again be methanol, in a preheating module 6 with four plate packs 7 to a start temperature of the catalytic exothermic reaction of acetylene to ethylene and the acetylene in the feed is hydrogenated in a downstream reaction module 8.

The gas in which the acetylene has been hydrogenated leaves the reaction module 8 of the reactor 2 via line 9 as ethylene product having the desired purity or the ethylene is passed to further purification steps not shown in the figure. The preheating module 6 and the reaction module a are arranged in a joint reactor vessel 10. The preheating module 6 contains inert particles and the reaction module 8 contains catalyst particles between the metal plates.

An advantageous application of the reactor of the invention will be demonstrated by means of an example.

EXAMPLE 1

Use in Ethylene Plants for Acetylene Hydrogenation

The hydrogenation of $C_2H_2$ has hitherto been carried out using reactors in which straight-tube heat exchangers with catalyst in the tubes provide the necessary cooling. Such reactors for an ethylene plant having an annual ethylene production capacity of about 600,000 tonnes have the following characteristic data:

Dimensions: 2 reactors of 4.5 mØ×13.8 m each, of these 1 reactor as 100% backup

Weight: each about 138 tonnes

Material: carbon steel

Reactors according to the invention for a plant having a product output of 600,000 tonnes per annum have, for example, the following data:

Dimensions: 2 reactors of 3.8 mØ×16 m each, of these 1 reactor as 100% backup

Weight; about 100 tonnes, of this about 80 tonnes of carbon steel, about 20 tonnes of stainless steel Material: Outer wall: carbon steel, plates: stainless steel The trend towards ever larger ethylene plants continues. Annual production outputs of 1,000,000 tonnes per line are being sought. However, in the case of a conventional reactor for $C_2H_2$ hydrogenation, the constructability limit is reached at a production capacity of about 600,000 tonnes per annum. If it is necessary at this point to go to multiple lines, this incurs considerable additional costs because, apart from the parallel reactors themselves, additional piping, regulators and controls for uniform throughput through all reactors are necessary. In the plate-exchanger reactor, the available volume is utilized much more efficiently, so that, for the same external dimensions, an about 40% higher catalyst volume can be accommodated and cooled in a plate-exchanger reactor than in a conventional reactor. Thus, even without the on-site assembly which is possible in principle, an about 40% higher throughput can be achieved in the case of plate-exchanger reactors, i.e. about 840,000 tonnes per annum of ethylene instead of 600,000 tonnes per annum. On-site assembly also makes possible an even higher ethylene output using only one reactor for the hydrogenation of $C_2H_2$.

A conventional reactor of this type requires material weighing about 140 tonnes. The heaviest individual parts are the tube plates which each weigh over 20 tonnes. These tube plates are dispensed with in the reactor of the inventions so that this alone saves material and weight. A reactor according to the invention for production of 600,000 tonnes of ethylene per annum weighs only about 80 tonnes. In addition, further advantages result from a lower pressure drop in the gas path and a shorter downtime when replacing the catalyst.

The invention is useful for a wide variety of generally known processes: CO conversion, epoxidation olefins for the production of olefin epoxides, selective hydrogenation of hydrocarbons (for example, of $C_2H_2$ to $C_2H_4$), nonselective hydrogenation of hydrocarbons (for example, of $C_2H_2$ to $C_2H_6$), synthesis of methane, synthesis of methanol, Claus reaction, direct oxidation of $H_2S$ to elemental sulfur, Fischer-Tropsch synthesis, oxidation of $SO_2$ to $SO_3$, and synthesis of $NH_3$. Referring to Ullman's Encyclopedia, these processes are further described in the following table:

| Claim | Volume | Year | Pages |
| --- | --- | --- | --- |
| 7 | A2 | 1985 | 179–180 |
|   | A5 | 1986 | 211 |
|   | A12 | 1989 | 185, 238–243 |
|   | A13 | 1989 | 317–321, 376–377 |
| 8 | A9 | 1987 | 534–542 |
| 9 | A1 | 1958 | 128 |
|   | A10 | 1987 | 83 |
|   | A13 | 1989 | 487–494 |
| 10 | A13 | 1989 | 487–494 |
| 11 | A13 | 1989 | 405–406 |
| 12 | A13 | 1989 | 405–406 |
| 13 | A25 | 1994 | 571 |
| 14 | A25 | 1994 | 523 |

-continued

| Claim | Volume | Year | Pages |
| --- | --- | --- | --- |
| 15 | A13 | 1989 | 405–406 |
| 16 | A25 | 1994 | 697–698 |
| 17 | A2 | 1985 | 179–180 |
|   | A5 | 1986 | 211 |
|   | A12 | 1989 | 185, 238–248 |
|   | A13 | 1989 | 376–377 |

The preceding examples can be repeated with similar success by substituting the generically or specifically described reactants and/or operating conditions of this invention for those used in the preceding examples. Also, the preceding specific embodiments are to be construed as merely illustrative, and not limitative of the remainder of the disclosure in any way whatsoever.

The entire disclosure of all applications, patents and publications, cited above and below, and of corresponding German application 198 51 109.4, are hereby incorporated by reference.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A reactor comprising:
   at least one reactor vessel for carrying out reactions having an enthalpy change,
   coolable dividing walls positioned within said reactor vessel, said coolable dividing walls defining a plurality of compartments between said walls in which particulate catalyst solids are retained, wherein said coolable dividing walls comprise metal plates having means defining hollow or intermediate spaces in the form of channels within said metal plates for accommodating and conveying a heat transfer medium,
   wherein said plates are in the form of at least one metal plate pack, and
   an inlet for introducing fluid reactant into said reactor vessel and an outlet for removing fluid product from said reactor vessel wherein said inlet and outlet are positioned to provide for fluid reactant to flow through said compartments in parallel.

2. A reactor according to claim 1, wherein the metal plate packs comprise flat, parallel, plates.

3. A reactor according to claim 1, comprising a plurality of metal plate packs arranged next to one another in the reactor vessel so as to form a module of plate packs through which feed gas may flow in parallel.

4. A reactor according to claim 3, comprising a plurality of modules in the same reactor vessel, arranged above one another.

5. A reactor according to claim 1, wherein the metal plate packs are arranged vertically.

6. A reactor according to claim 2 wherein the metal plate packs comprise curved plates arranged in concentric cylinders.

7. A reactor according to claim 4 comprising a plurality of modules arranged in a plurality of serially connected reactor vessels.

8. A reactor according to claim 1, wherein said dividing walls contain a heat exchange fluid in said channels.

\* \* \* \* \*